(12) United States Patent
Wagner et al.

(10) Patent No.: US 6,859,277 B2
(45) Date of Patent: Feb. 22, 2005

(54) PARTICLE COUNTER WITH STRIP LASER DIODE

(75) Inventors: Gregg A. Wagner, Boulder, CO (US); Thomas Bates, Westminster, CO (US)

(73) Assignee: Particle Measuring Systems, Inc., Boulder, CO (US)

( * ) Notice: Subject to any disclaimer, the term of this patent is extended or adjusted under 35 U.S.C. 154(b) by 389 days.

(21) Appl. No.: 10/228,577

(22) Filed: Aug. 27, 2002

(65) Prior Publication Data

US 2004/0042008 A1 Mar. 4, 2004

(51) Int. Cl.[7] .............................................. G01N 21/00
(52) U.S. Cl. ..................................... 356/337; 356/338
(58) Field of Search ................................. 356/335–338

(56) References Cited

U.S. PATENT DOCUMENTS

| | | | | |
|---|---|---|---|---|
| 4,596,464 A | * | 6/1986 | Hoffman et al. | 356/336 |
| 5,092,675 A | * | 3/1992 | Sommer | 356/338 |
| 5,282,151 A | | 1/1994 | Knollenberg | |
| 5,402,438 A | * | 3/1995 | Tanuma | 372/99 |
| 6,628,386 B2 | | 9/2003 | Davis et al. | |

FOREIGN PATENT DOCUMENTS

WO  WO 01/27686 A1  4/2001

* cited by examiner

Primary Examiner—Zandra Smith
Assistant Examiner—Kara Geisel
(74) Attorney, Agent, or Firm—Patton Boggs LLP

(57) ABSTRACT

A fluid particle counter comprising an inlet jet tip producing an air flow, a strip laser diode producing a laser beam, and a beam shaping system that includes an aspheric collimating lens, an achromatic spherical lens, a cylinder lens, and a series of cascading apertures. A retarder rotates the polarization so that the TE mode is along the direction of fluid flow. The optical system is designed so that along the flow axis the laser beam is single mode, while the multimodes due to the strip laser are constrained to the dimension perpendicular to the flow. The beam is pinched to a 35 micron waist and has a Gaussian profile along the flow direction which permits locating the beam within 3.5 mm of the flow tip while preventing stray light scattering from the tip. The beam profile along the axis perpendicular to the flow is closer to a square wave than a Gaussian. The particle counter output is substantially free of all noise except noise created by light scattered from molecules of the fluid, even for volumetric particle counters.

36 Claims, 5 Drawing Sheets

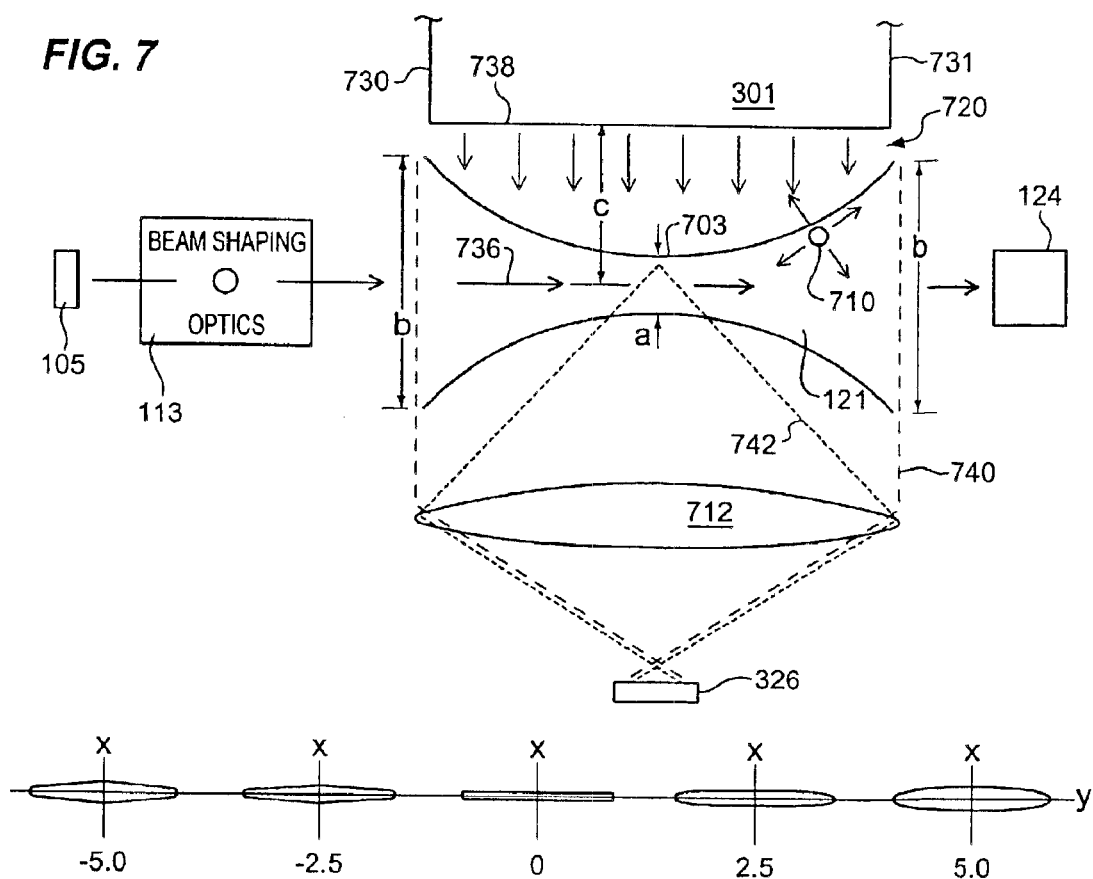
FIG. 7
FIG. 8
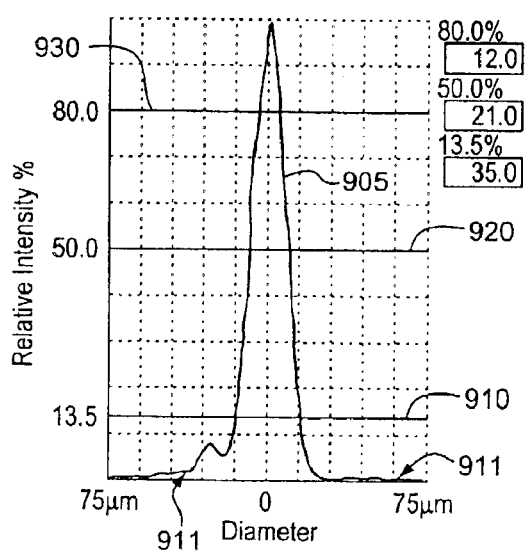
FIG. 9
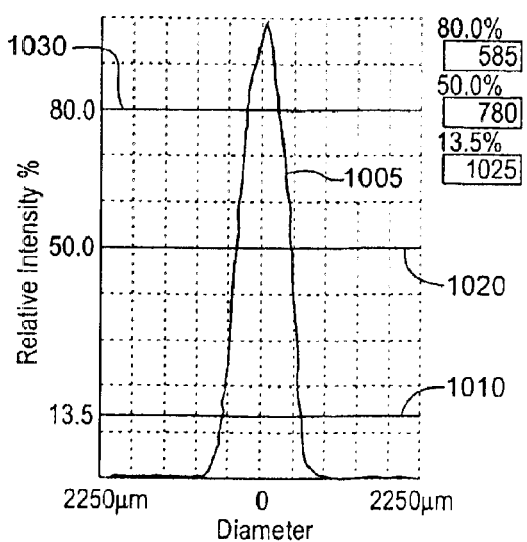
FIG. 10

PARTICLE COUNTER WITH STRIP LASER DIODE

BACKGROUND OF THE INVENTION

1. Field of the Invention

The invention in general relates to systems which utilize light scattering principles to detect and count undesirable single particles in fluids, referred to in the art as light scattering particle counters, and more particular to such a particle counter that utilizes a laser diode light source.

2. Statement of the Problem

The principles of light scattering are widely used for detecting and analyzing particles in or of a fluid. The present invention relates to the science of utilizing the principles of light scattering to detect and measure the size of individual particles suspended in a fluid. Each particle that is detected is counted, and an indication of the number of particle counts within a channel, with each channel corresponding to a particular size range, is provided. For particle counters to operate effectively, the density of particles in the fluid must be very small—indeed, the particles are generally considered to be contaminants. It is important to distinguish the science of particle counting from other scientific fields, such as photometry and cytometry, which also utilize scattered light, but in which the density of the particles in the fluid is relatively large; often it is the particles of the fluid itself that are detected and analyzed. These latter systems rely on collecting scattered light from thousands, millions, and even billions of particles; therefore, their principles of operation are very different from the principles used in particle counters.

Particle counters are generally used to detect contaminants in extremely pure fluids, such as those used in high tech electronics and the pharmaceutical industry. Generally, small samples of the fluids used in the manufacturing processes are diverted to the particle counters, which sound an alarm if the number and/or size of the particles detected is above a predetermined threshold. Since a small sample of the manufacturing fluid is generally not completely representative of the entire volume of the manufacturing fluid, statistics is used to extrapolate the state of the manufacturing fluid from the sample. The larger the sample, the more representative it is, and the more quickly an accurate determination of the number and size of particles in the manufacturing fluid can be made. Thus, It is desirable for a particle counter to detect particles as small as possible, as fast as possible, in as large a sample as possible.

Physical constraints require tradeoffs between the above goals. For example, sample volume and speed usually must be sacrificed to detect smaller particles. This is a direct result of the fact that, for particles to be detected in a particular fluid, the fluid must be constrained to flow through the monitoring region of a particle counter. Physical objects, such as nozzles and flow tubes, must be used to direct the fluid flow to the particle counter monitoring region. If it is desired to detect the particles in the entire sample flow, then scattered light from the entire sample flow must be collected. This generally results in light scattered from the physical constraining objects, such as a nozzle or flow tube, also being collected, which light creates noise in the output. The noise prevents detection of extremely small particles. This noise can be avoided by detecting particles in only a small portion of the sample flow. Particle counters that attempt to count all the particles in a fluid sample are generally referred to as volumetric particle counters, and particle counters that detect particles in only a small portion of the fluid flow are generally referred to as in-situ particle counters.

The word in-situ in Latin literally means in the natural state. That is, ideally, it refers to measurements unaffected by the measurement instrumentation. In an in-situ system, to be unaffected from the constraining elements, the detected particles must be far from the constraining elements, and only particles in a small fraction of the sample fluid flow are detected. In-situ systems commonly process 5% or less of the sampled fluid. An in-situ single pass particle counter is disclosed in U.S. Pat. No. 5,459,569, issued Oct. 17, 1995 to Knollenberg et al., which patent is hereby incorporated by reference. As a result of measuring only a selected fraction of fluid flow, however, in-situ systems take more time to achieve a statistically significant determination of the fluid cleanliness level or fluid quality. When measuring particle contamination levels in a clean room environment, this extended measurement time generally incurs the risk that an unacceptably high level of airborne or liquid particle concentration could go undetected for substantial time periods, thereby allowing a large number of manufactured parts to be produced under unacceptably "dirty" conditions. This situation can lead to substantial economic loss owing to the waste of time and production materials in the affected facility.

Since it is practically impossible to actually measure 100% of the particles carried by flowing fluid, herein the term "volumetric" generally corresponds to systems which measure 90% or more of the particles flowing through a measurement device. Volumetric particle measurement systems generally provide the advantage of measuring a greater volume of fluid, whether liquid or gas, within a fixed time period, thereby enabling a more rapid determination of a statistically significant measure of fluid quality. In the case where the particle concentration exceeds a predetermined permissible limit, this more rapid fluid processing generally enables a defective manufacturing process to be halted more quickly and more economically than would be possible employing in-situ measurement systems. However, as indicated above, volumetric measurement systems generally experience more noise than do in-situ systems because the efforts expended to control the location and flow characteristics of the fluid being analyzed generally perturbs the characteristics being measured to a greater extent than does in-situ measurement. One example of a trade-off between measurement completeness and interference with measurement data is that which arises when establishing the proximity of placement of a fluid inlet nozzle to a laser beam. Generally, both the completeness of the measurement, i.e., the percentage of sample flow measured and the interference with this measurement, increase with increasing proximity of the nozzle to the laser beam.

In various circumstances, there may be measurement processes having characteristics which are intermediate between in-situ and volumetric processes. Thus, where in-situ measurement generally corresponds to particle measurement within 5% or less of fluid transported through a measurement device, and volumetric measurement generally corresponds to analysis of 90% or more of such fluid, it will be recognized that measurement processes may be configured to process 10%, 30%, 50%, or other percentages in between the levels associated with in-situ and volumetric operation. Accordingly, herein, the term "non-in-situ" measurement generally corresponds to measurement of a proportion of fluid equal to more than 5% of total fluid flow.

In the field of particle counting, the use of high power illumination generally enhances particle detection.

Specifically, higher power levels generally enable the detection of smaller particles than lower power systems. Higher power levels also generally permit particles of a given size to be detected more quickly. Thus, lasers are generally used as the light source in particle counters. Laser particle counters are of two types: intracavity particle counters in which the sample volume passes through the laser cavity, and extracavity particle counters, usually referred to as "single pass" particle counters, in which the sample volume is located outside the laser cavity. Locating particle-containing fluid flow within the cavity of the laser illuminating the particles provides for higher illumination power levels than are available in single pass laser systems, because, to maintain the lasing action, only a limited amount of optical energy is allowed to pass out of the cavity. A state-of-the-art in-cavity laser particle measurement system is disclosed in U.S. Pat. No. 5,889,589, issued Mar. 30, 1999 to Jon C. Sandberg, which patent is hereby incorporated by reference herein. However, in such particle counters, significant fluid flow through the laser cavity tends to modulate the characteristics of the laser cavity, thereby introducing undesired noise due to the medium, e.g., the air molecules. For this reason, fluid flow rates are commonly reduced when employing in-cavity systems to minimize the introduction of the cavity modulation-related noise. Conventional laser pumping cavities also have cavity power fluctuations greater than 30% short term and 50% long term caused by such things as thermal effects, air density changes, and particulate contamination of the laser cavity. Further, it is difficult to maintain calibration with such power level changes, because not all noise levels track linearly with power. This results in calibration errors occurring in most systems as the power level decreases. For this reason, cavity systems need to be purged regularly, and the systems need to be disassembled regularly to mechanically clean them. Locating a fluid flow containing particles for counting and measurement outside a laser cavity in a "single pass" laser system utilizing a solid-state laser diode generally avoids all of these problems and permits larger fluid samples to be monitored, but at the expense of much lower available laser power.

The power available in particle counters that utilize laser diodes to detect particles in fluid is also limited by multimode effects which necessarily arise in large laser diodes. The presence of multiple modes in a laser beam energy spectrum makes it extremely difficult to shape the beam. Further, in multiple mode light sources, light noise resulting from spontaneous emission occurs and is difficult to eliminate. Thus, all known commercial particle counters that utilize laser diodes to detect and measure particles in fluids have, up until now, been limited to single mode systems, typically the fundamental transverse electromagnetic mode, referred to as the $TEM_{00}$ mode. As known in the art, the light from laser diodes can be limited to a single mode by limiting their size. However, limiting the size of the laser diodes also limits their power.

Accordingly, there is a need in the art for a particle counter system and method which provides high power illumination in a low noise environment and which produces a scattered light energy spectrum which is readily convertible into particle measurement data. Further, to accomplish this in a non-in-situ system would be highly advantageous.

SUMMARY OF THE INVENTION

The present invention advances the art and helps to overcome the aforementioned problems by providing a particle counter utilizing a laser diode which provides a high power beam in a single pass, low noise system for rapid detection and measurement of small particles.

The invention provides a particle counter that utilizes a strip laser diode. Several breakthroughs in employing these large diodes have been made. In one, the multimodes that inherently occur with such a diode are constrained to a dimension perpendicular to the fluid flow. This permits the beam along the fluid flow to be focused to a very small width. In another breakthrough, several different lens combinations have been found to be effective in controlling the beam. In one, an aspheric collimating lens, an achromatic spherical lens, and a cylinder lens are used in combination. In another embodiment, an aspheric collimating lens and two cylinder lenses are used in combination. Another breakthrough permits the light noise due to spontaneous emission to be essentially eliminated.

The invention provides a device for optically detecting an unconstrained particle suspended in a flowing fluid, the device comprising: a sample chamber having a fluid inlet and a fluid outlet; a strip laser diode producing a laser beam; a beam shaping system directing the laser beam at the flowing fluid in the sample chamber; a light collector located to collect light scattered by the particle in the sample chamber, the collector producing an electric signal characteristic of the scattered light; and an output device communicating with the collector to provide an output characteristic of the particle detected in the fluid in the sample chamber. Preferably, the fluid is a gas. Preferably, 10% or more of the particles suspended in the fluid passing through the sample chamber are detected; more preferably, 30% or more of the particles suspended in the fluid passing through the sample chamber are detected. More preferably, 50% or more of the particles suspended in the fluid passing through the sample chamber are detected; and most preferably, 80% or more of the particles suspended in the fluid passing through the sample chamber are detected. In the preferred embodiment, the device is a volumetric particle counter. Preferably, the beam shaping system comprises a lens. Preferably, the lens comprises an aspheric collimating lens, an achromatic spherical lens, and a cylinder lens. In another embodiment, the lens comprises an aspheric collimating lens and two cylinder lenses. Preferably, the fluid flows in a first direction, the laser beam is single mode in a dimension substantially along the first direction. Preferably, the fluid flows in a first direction, the laser beam includes multiple modes in a dimension substantially in a direction perpendicular to the first direction. Preferably, the fluid flows along a first axis, and the energy distribution of the laser beam substantially along the first axis, in terms of distance from the center of the laser beam versus relative intensity as compared to the intensity at the center, is Gaussian. Preferably, the fluid flows along a first axis, and the energy distribution of the laser beam substantially along a second axis perpendicular to the beam and the first axis, in terms of distance from the center of the laser beam versus relative intensity as compared to the intensity at the center, is more uniform than a Gaussian distribution. Preferably, the fluid flows along a first axis, and the $1/e^2$ width of the laser beam in the direction of the first axis, at a first point within the fluid flow, is 75 microns or less. More preferably, the width is 50 microns of less. Most preferably, the width is 40 microns or less. Preferably, at a second point at the edge of the fluid flow, the $1/e^2$ width of the laser beam in a direction parallel to the first axis is 200 microns or less. More preferably, the width at the second point is 175 microns or less. Most preferably, the width at the second point is 150 microns or less. Preferably, the fluid inlet comprises an inlet jet tip from which the fluid flows, and the separation distance of the center of the laser beam from the inlet jet tip is 7 mm or less. More preferably, the separation distance is 5 mm or less. Most preferably, the separation distance is 4 mm or less. Preferably, the strip laser diode has a power of 1 watt or greater. More preferably, the strip laser diode has a power of 2 watts or greater. Preferably, the output is substantially free of noise greater than the noise created by light scattered from molecules of the fluid.

In another aspect, the invention provides a device for optically detecting an unconstrained particle suspended in a flowing fluid, the device comprising: a fluid inlet for producing a fluid flow; a strip laser diode producing a laser beam; a beam shaping system directing the laser beam at the fluid flow; a light collector located to collect light scattered by the particle in fluid flow, the collector producing an electric signal characteristic of the scattered light; and an output device communicating with the collector to provide an output characteristic of the particle detected in the fluid.

In a further aspect, the invention provides a device for optically detecting an unconstrained particle suspended in a flowing fluid, the device comprising: a sample chamber having a fluid inlet and a fluid outlet; a laser diode producing a laser beam, the laser diode having at least one dimension 10 microns or larger; a beam shaping system directing the laser beam at the flowing fluid in the sample chamber; a light collector located to collect light scattered by the particle in the sample chamber, the collector producing an electric signal characteristic of the scattered light; and an output device communicating with the collector to provide an output characteristic of the particle detected in the fluid in the sample chamber. Preferably, the dimension is 50 microns or greater. More preferably, the dimension is 100 microns or greater.

In yet a further aspect, the invention provides a device for optically detecting an unconstrained particle suspended in a flowing fluid, the device comprising: a fluid inlet for flowing the fluid in a first direction; a laser producing a laser beam having multiple modes; a beam shaping system directing said multiple mode laser beam at said flowing fluid with said multiple modes constrained to a dimension along a second direction substantially perpendicular to said first direction; a light collector located to collect light scattered by the particle in the flowing fluid, the collector producing an electric signal characteristic of the scattered light; and an output device communicating with the collector to provide an output characteristic of the particle detected in the fluid flow. Preferably, the beam shaping system comprises a one-half wave plate. Preferably, the laser comprises a strip laser diode.

The invention also provides a method for optically detecting an unconstrained particle suspended in a fluid, the method comprising: flowing the fluid containing an unconstrained particle; providing a strip laser diode producing a laser beam having multiple modes; directing the laser beam at the fluid flow; collecting light-scattered by the particle in the fluid; and providing an output based on the collected light scattered by the particle detected in the flowing fluid. Preferably, the fluid flows substantially along a first direction, and providing and directing comprises controlling the laser beam so that the multiple modes occur in a dimension along a second direction perpendicular to the first direction and the direction of the laser beam. Preferably, said providing and directing comprises providing said laser beam and directing it so that said laser beam is single mode in a first dimension along said first direction. Preferably, the directing comprises focusing the laser beam with at least two lenses selected from the group consisting of an aspheric collimating lens, an achromatic spherical lens, and a cylinder lens. Preferably, the directing, collecting and providing an output are performed such that the output is substantially free of noise greater than the noise created by light scattered from molecules of the fluid.

The invention enables much larger, and therefore more powerful, laser diodes to be used effectively in a fluid particle counter. As will be seen in more detail below, the invention teaches how to control noise from spontaneous emission while examining a large portion of the fluid flow. While the system permits high-powered, low noise volumetric systems that were not previously possible, it should be understood that the invention is not limited to volumetric systems. The invention can be used to advantage in any particle counter, including non-in-situ and in-situ systems. The above and other advantages of the present invention may be better understood from a reading of the following description of the preferred exemplary embodiments of the invention taken in conjunction with the drawings in which:

BRIEF DESCRIPTION OF THE DRAWINGS

FIG. 7 is a side diagrammatic view of a portion of a laser beam positioned next to an inlet jet tip according to a preferred embodiment of the present invention;

FIG. 8 illustrates a head-on view of the laser beam at five positions as it passes the inlet jet tip;

FIG. 9 is a graph showing the energy distribution of the laser beam along the X-axis in terms of distance from the center of the laser beam versus relative intensity; and FIG. 10 is a graph showing the energy distribution of the laser beam along the Y-axis in terms of the distance from the center of the laser beam versus relative intensity.

DETAILED DESCRIPTION OF THE PREFERRED EMBODIMENT

In this disclosure, the term light is not limited to visible radiation but is used in a broad sense meaning any electromagnetic radiation. The terms in-situ and volumetric are used as described in the Background Of The Invention above. It is also noted that this disclosure is limited to fluid particle counters, which is a term of art. There are particle counters that detect particle counters in a vacuum. Because there is no fluid present, or rather any fluid present is rarified as compared to normal fluids, problems associated with fluid flow, light scattering from the fluid and the apparatus used to control the fluid flow are absent and the physics of such particle counters is significantly different than that of fluid particle counters. Further, it should be noted that particle counters as disclosed herein are designed to be able to detect single particles which are unconstrained in a flowing fluid as distinguished from other systems that detect and analyze the particles of the fluid itself, clouds of particles suspended in a fluid, or particles which are constrained in the fluid, such as constrained to flow in a single line past a light beam. Those skilled in the art recognize that it is a much more difficult task to detect and size single particles flowing unconstrained in a fluid; therefore, the art of particle counting involves different technology than these other particle detection and analysis systems.

Figure 1:
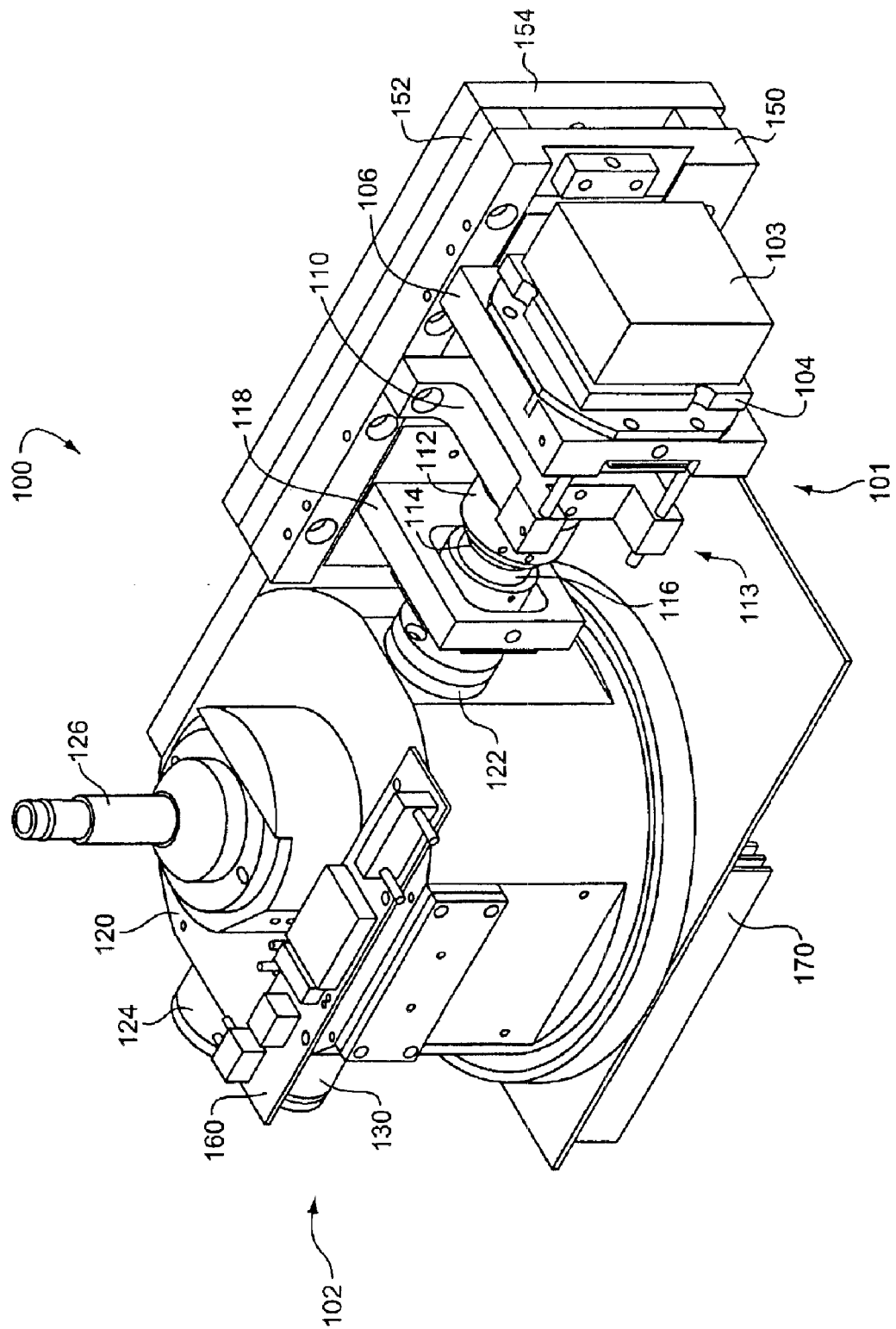
FIG. 1 is a perspective view of a particle counter according to a preferred embodiment of the present invention.
Figure 2:
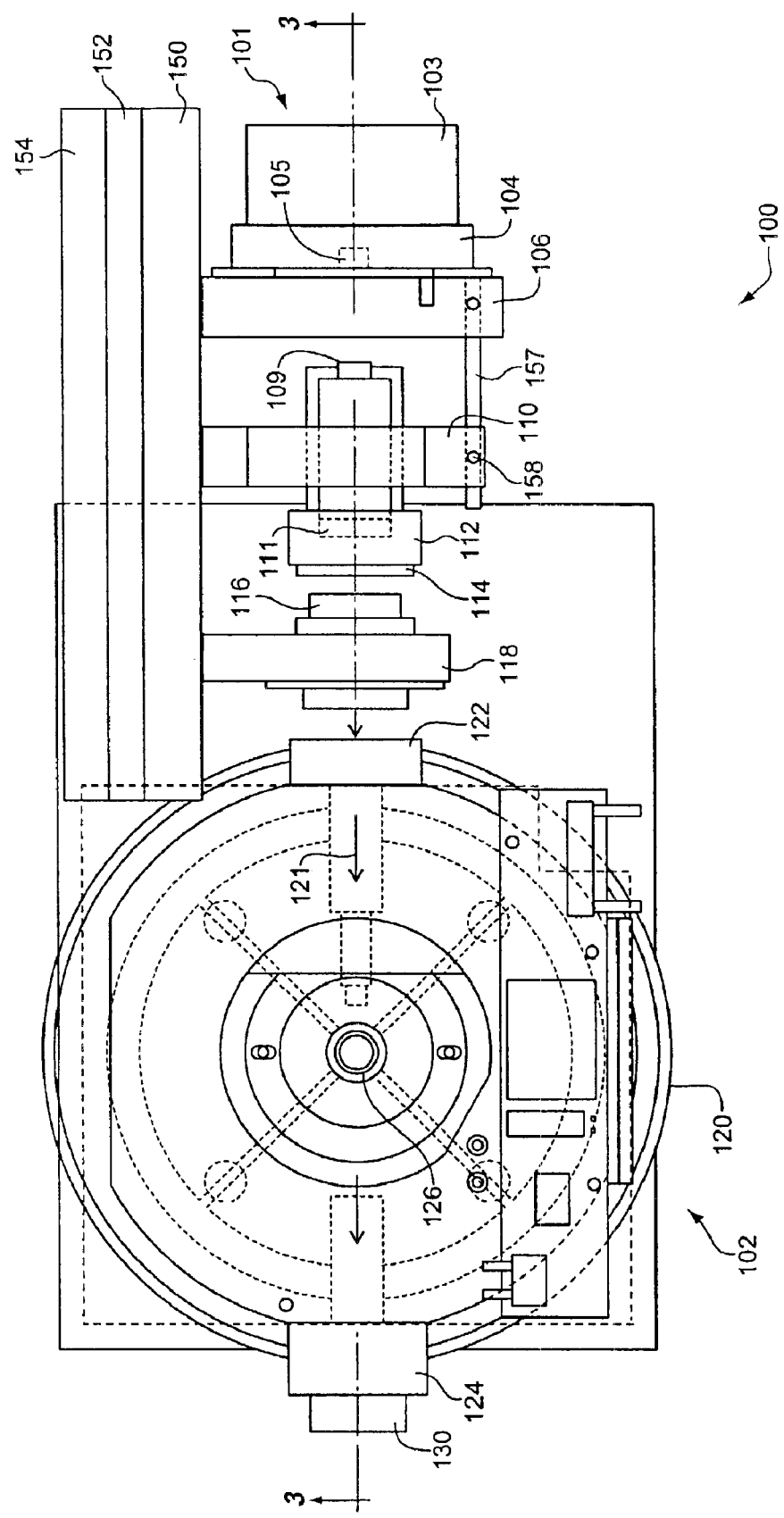
FIG. 2 is a top view of the system shown in FIG. 1.

FIG. 1 is a perspective view of a particle counter 100 according to the invention. FIG. 2 is atop view of particle counter 100 which has been simplified so as to more clearly illustrate the key elements of the invention. Considering both FIGS. 1 and 2, particle counter 100 includes optics assembly 101 and flow chamber assembly 102. Optics assembly 101 includes laser heat sink 103, laser assembly 104 including diode laser 105, laser mount assembly 106, and beam shaping optics 113. Beam shaping optics 113 preferably includes first lens 109, first and second lens mount assembly 110, second lens 111, retarder mount assembly 112, retarder 114, third lens 116, third lens mount assembly 118, and laser aperture assembly 122. Optics assembly 101 is mounted on an optics rail 150. Optics rail 150 and flow chamber assembly 102 are mounted on a mounting plate 154. Optics rail 150 and mounting plate 154 are separated by a spacer plate 152. As known in the art, a variety of hardware, such as rod 157 and screw 158, are used to support the components of optics assembly 101 and adjust the relative positions of the parts, though only a few are shown; otherwise, the drawing becomes confusingly complex. Flow chamber assembly 102 includes flow chamber housing 120, beam stop assembly 124, fluid inlet assembly 126, fluid outlet assembly 130, circuit board 160, and collector electronics heat sink 170. Arrows 121 indicate the direction and path of the laser beam. All housing parts, supports, connectors and adjusters of particle detector 100 are preferably made of aluminum with any surfaces that may be exposed to light being black anodized and coated with an infrared absorbing paint, though any other suitable materials may be used.

A key aspect of the invention is that laser 105 is a strip laser diode which produces much more power than any laser diode used in prior art particle counters for counting particles in fluids. In FIG. 2, laser diode 105 is being viewed from the long "strip" side and its size is exaggerated; otherwise, it would be difficult to draw clearly. Preferably, the length in the vertical direction in FIG. 2 is 100 microns, while the width extending into and out of the paper is 1 micron, though the invention contemplates that other sizes of strip laser diodes may be used. To develop significant power, at least one dimension of the laser diode should be 10 microns or greater, and more preferably 50 microns or greater. Most preferably, it is 100 microns or greater. The strip laser diode according to the invention has a power of 1 watt or greater, and more preferably 2 watts or greater. A typical strip laser diode that may be used is the model S-79 series made by Coherent Semiconductor Group, 5100 Patrick Henry Drive, Santa Clara, Calif. 95054. The 1200C-100-x which produces 1200 milliwatts (mW) of power or the 2000C-150-x which produces 2000 mW of power are currently the most preferred strip laser diodes. These lasers have a center wavelength of 780 to 800 nanometers, though other wavelengths may be used. Preferably, a laser of from 1 watt to 5 watts of power is used in particle counter 100 according to the invention.

Figure 3:
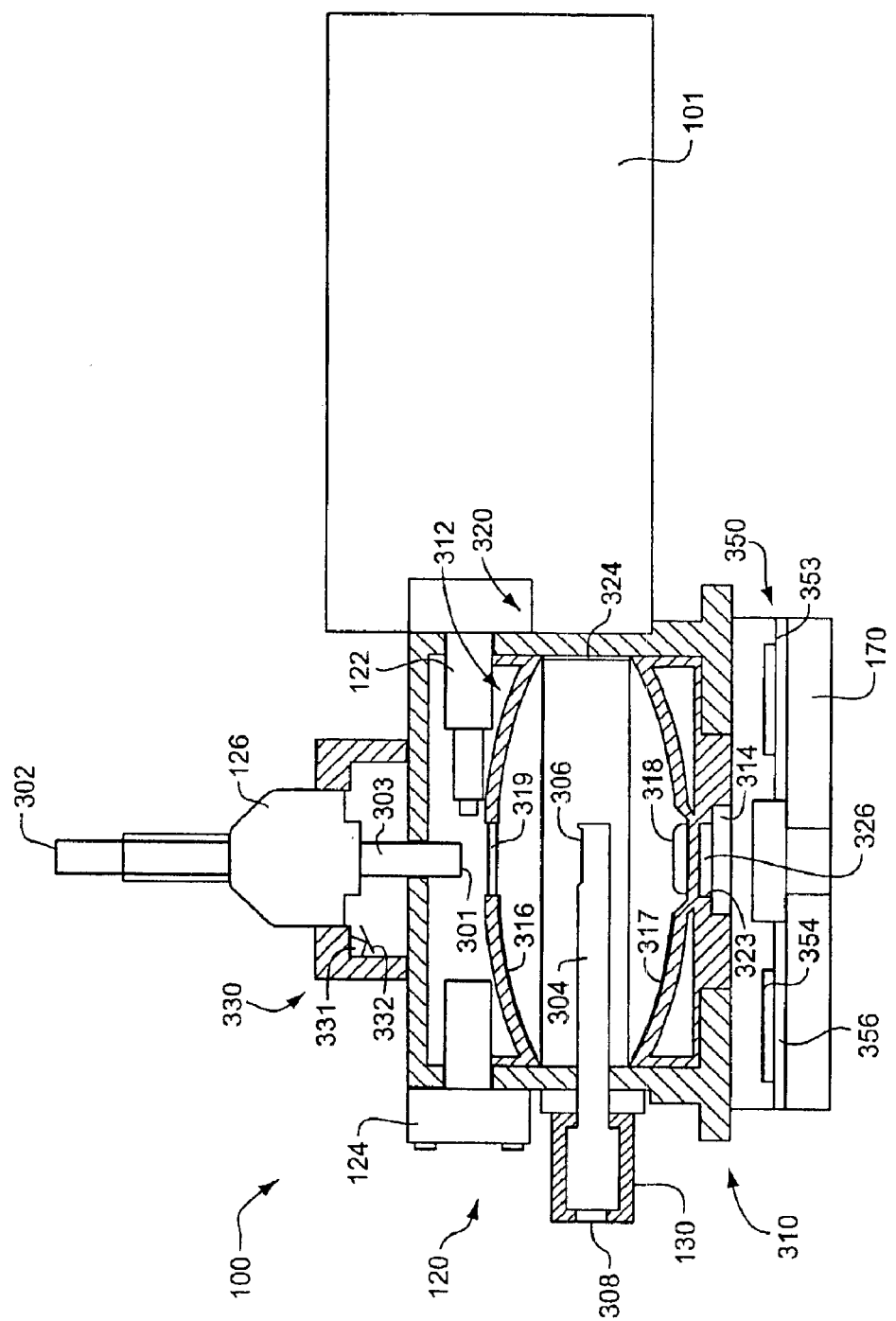
FIG. 3 is a simplified and partially modified cross-section of the system of FIG. 1 taken through the lines 3—3 of FIG. 2.

Because of its size, laser 105 has multiple modes in the vertical direction in FIG. 2. In the direction into the paper in FIG. 2, it has a single mode. A further key aspect of the invention lies in beam shaping optics 113 and the method by which the beam shaping optics manipulates the laser beam to avoid significant noise and to permit the collecting optics to accurately detect and measure particles. First lens 109 is preferably an aspheric collimating lens, second lens 111 is preferably an achromatic spherical lens, and third lens 116 is preferably a cylinder lens. First lens 109 and second lens 111 together preferably shape laser beam 121 along an axis into and out of the paper in FIG. 2, which is the vertical axis in FIGS. 3 and 7. We shall call this the "first axis", or "X-axis", herein. The third lens, that is the cylindrical lens, preferably corrects astigmatism of the optics focuses the height of the beam, which is the vertical axis in FIG. 2, the axis into and out of the paper in FIGS. 3 and 7, referred to as the "Y-axis" herein, to match the height of inlet jet 301 (FIG. 3). The cylinder lens is important because strip laser diode 105 has a considerable amount of astigmatism and the cylinder lens corrects for this and controls the Y-axis beam shape. Other lens combinations may also be used. Further, as known in the art, for every lens, there is a mirror that functions equivalently. Thus, mirrors or other equivalent optical structures may be used. For example, the achromatic lens may be replaced by a second cylindrical lens. However, the preferred embodiment has the advantage that the alignment of the optics is less critical. Using two cylindrical lenses usually would require that the first lens be rotationally oriented to the facet prior to focusing and rotating the second lens. In the preferred embodiment, no adjustment is required for achromatic spherical lens 111, and the cylindrical lens may be rotationally aligned and focused. Additionally, using the achromatic lens also corrects a portion of the spherical aberrations, which helps to further reduce the beam waist, i.e., the minimum dimension of the beam along the X-axis, which is the dimension "a" in FIG. 7. As known in the art, an optimized specification of the beam shaping optics may be obtained by inserting the above information in an optics design software program, such as Zemax™ produced by Focus Software, Inc. or Code-V produced by Optical Research Corporation. A complete specification of the beam shaping optics produced in such a manner is given in Table I.

TABLE I

GENERAL LENS DATA:

| | |
|---|---|
| Surfaces | 11 |
| Stop | 1 |
| System Aperture | Object Space NA = 0.0697565 |
| Glass Catalogs | schott misc OLD_CORN |
| Ray Aiming | Off |
| Apodization | Uniform, factor = 0.00000e+000 |
| Effective Focal Length | −1.487864 (in air) |
| Effective Focal Length | −1.487864 (in image space) |
| Back Focal Length | 105.4692 |
| Total Track | 127.0765 |
| Image Space F/# | 19.66491 |
| Paraxial Working F/# | 32.46918 |

TABLE I-continued

| | |
|---|---|
| Working F/# | 37.03974 |
| Image Space NA | 0.02153427 |
| Object Space NA | 0.0697565 |
| Stop Radius | 0.03783042 |
| Paraxial Image Height | 0 |
| Paraxial Magnification | 0 |
| Entrance Pupil Diameter | 0.07566084 |
| Entrance Pupil Position | 0 |
| Exit Pupil Diameter | 1.361227 |
| Exit Pupil Position | −32,4992 |
| Field Type | Angle in degrees |
| Maximum Field | 0 |
| Primary Wave | 0.68 |
| Lens Units | Millimeters |
| Angular Magnification | 0 |
| Fields | 1 |

| Field Type: | Angle in degrees | | |
|---|---|---|---|
| # | X-Value | Y-Value | Weight |
| 1 | 0.000000 | 0.000000 | 1.000000 |

| Vignetting Factors: | | | | |
|---|---|---|---|---|
| # | VDX | VDY | VCX | VCY |
| 1 | 0.000000 | 0.000000 | 0.000000 | 0.000000 |

| Wavelengths | 1 |
|---|---|
| Units | Microns |

| # | Value | Weight |
|---|---|---|
| 1 | 0.680000 | 1.000000 |

SURFACE DATA SUMMARY:

| Surf | Type | Comment | Radius | Thickness | Glass | Diameter | Conic |
|---|---|---|---|---|---|---|---|
| OBJ | STANDARD | | Infinity | 0.541 | | 0 | 0 |
| STO | PARAX_XY | | — | 0.1319285 | | 0.07566084 | — |
| 2 | STANDARD | | Infinity | 0.001394947 | | 0.1 | 0 |
| 3 | STANDARD | | Infinity | 0.25 | BK7 | 2.55295 | 0 |
| 4 | STANDARD | | Infinity | 2.55317 | | 2.465709 | 0 |
| 5 | EVENASPH | | 19.9223 | 2.94 | C0550 | 4.96 | 0 |
| 6 | EVENASPH | | −2.944996 | 2.5 | | 4.96 | −0.481104 |
| 7 | TOROIDAL | | Infinity | 2.5 | BK7 | 10 | 0 |
| 8 | STANDARD | | Infinity | 2.5 | | 10 | 0 |
| 9 | TOROIDAL | | 50 | 2.5 | BK7 | 10 | 0 |
| 10 | STANDARD | | Infinity | 111.2 | | 10 | 0 |
| IMA | STANDARD | | Infinity | | | 0.01458875 | 0 |

SURFACE DATA DETAIL:

| | |
|---|---|
| Surface OBJ | STANDARD |
| Scattering | None |
| Surface STO | PARAX_XY |
| X Power | 0 |
| Y Power | 16 |
| Scattering | None |
| Surface 2 | STANDARD |
| Scattering | None |
| Surface 3 | STANDARD |
| Scattering | None |
| Surface 4 | STANDARD |
| Scattering | None |
| Surface 5 | EVENASPH |
| Coeff on r 2 | 0 |
| Coeff on r 4 | −0.0042371 |
| Coeff on r 6 | 0.00063484 |
| Coeff on r 8 | −3.46526e−005 |
| Coeff on r 10 | 0 |
| Coeff on r 12 | 0 |
| Coeff on r 14 | 0 |
| Coeff on r 16 | 0 |
| Scattering | None |
| Surface 6 | EVENASPH |
| Coeff on r 2 | 0 |
| Coeff on r 4 | 2.89094e−005 |
| Coeff on r 6 | 3.76282e−005 |

TABLE I-continued

| | |
|---|---|
| Coeff on r 8 | −3.26442e−006 |
| Coeff on r 10 | 1.17572e−006 |
| Coeff on r 12 | 0 |
| Coeff on r 14 | 0 |
| Coeff on r 16 | 0 |
| Scattering | None |
| Surface 7 | TOROIDAL |
| Rad of rev. | −13.75 |
| Coeff on y^2 | 0 |
| Coeff on y^4 | 0 |
| Coeff on y^6 | 0 |
| Coeff on y^8 | 0 |
| Coeff on y^10 | 0 |
| Coeff on y^12 | 0 |
| Coeff on y^14 | 0 |
| Scattering | None |
| Surface 8 | STANDARD |
| Scattering | None |
| Surface 9 | TOROIDAL |
| Rad of rev. | 0 |
| Coeff on y^2 | 0 |
| Coeff on y^4 | 0 |
| Coeff on y^6 | 0 |
| Coeff on y^8 | 0 |
| Coeff on y^10 | 0 |
| Coeff on y^12 | 0 |
| Coeff on y^14 | 0 |
| Scattering | None |
| Surface 10 | STANDARD |
| Scattering | None |
| Surface IMA | STANDARD |
| Scattering | None |

COATING DEFINITIONS:

EDGE THICKNESS DATA:

| Surf | X-Edge | Y-Edge |
|---|---|---|
| OBJ | 0.541000 | 0.541000 |
| STO | 0.131929 | 0.131929 |
| 2 | 0.001395 | 0.001395 |
| 3 | 0.250000 | 0.250000 |
| 4 | 2.645966 | 2.645966 |
| 5 | 1.699261 | 1.699261 |
| 6 | 2.706630 | 3.647942 |
| 7 | 3.441312 | 2.500000 |
| 8 | 2.500000 | 2.750628 |
| 9 | 2.500000 | 2.249372 |
| 10 | 111.200000 | 111.200000 |
| IMA | 0.000000 | 0.000000 |

SOLVE AND VARIABLE DATA:

| | |
|---|---|
| Semi Diameter 2 | Fixed |
| Semi Diameter 3 | Fixed |
| Semi Diameter 4 | Fixed |
| Semi Diameter 5 | Fixed |
| Semi Diameter 6 | Fixed |
| Semi Diameter 7 | Fixed |
| Semi Diameter 8 | Fixed |
| Semi Diameter 9 | Fixed |
| Thickness of 10 | Variable |
| Semi Diameter 10 | Fixed |

INDEX OF REFRACTION DATA:

| Surf | Glass | Temp | Pres | 0.680000 |
|---|---|---|---|---|
| 0 | | 20.00 | 1.00 | 1.00000000 |
| 1 | | 20.00 | 1.00 | 1.00000000 |
| 2 | | 20.00 | 1.00 | 1.00000000 |
| 3 | BK7 | 20.00 | 1.00 | 1.51361483 |
| 4 | | 20.00 | 1.00 | 1.00000000 |
| 5 | C0550 | 20.00 | 1.00 | 1.60044174 |
| 6 | | 20.00 | 1.00 | 1.00000000 |
| 7 | BK7 | 20.00 | 1.00 | 1.51361483 |
| 8 | | 20.00 | 1.00 | 1.00000000 |
| 9 | BK7 | 20.00 | 1.00 | 1.51361483 |

TABLE I-continued

| | | | |
|---|---|---|---|
| 10 | 20.00 | 1.00 | 1.00000000 |
| 11 | 20.00 | 1.00 | 1.00000000 |

THERMAL COEFFICIENT OF EXPANSION DATA:

| Surf | Glass | TCE *1QE−6 |
|---|---|---|
| 0 | | 0.00000000 |
| 1 | | 0.00000000 |
| 2 | | 0.00000000 |
| 3 | BK7 | 7.10000000 |
| 4 | | 0.00000000 |
| 5 | C0550 | 0.00000000 |
| 6 | | 0.00000000 |
| 7 | BK7 | 7.10000000 |
| 8 | | 0.00000000 |
| 9 | BK7 | 7.10000000 |
| 10 | | 0.00000000 |
| 11 | | 0.00000000 |

F/# calculations consider vignetting factors and ignore surface apertures:

| | Wavelength: | 0.680000 | |
|---|---|---|---|
| # | Field | Tan | Sag |
| 1 | 0.0000, 0.0000 deg: | 26.5604 | 157.5999 |

GLOBAL VERTEX COORDINATES, ORIENTATIONS, AND ROTATION/OFFSET MATRICES:

| | Reference Surface: 1 | | | |
|---|---|---|---|---|
| Surf | R11 R21 R31 | R12 R22 R32 | R13 R23 R33 | X Y Z |
| 0 | 1.000000 0.000000 0.000000 | 0.000000 1.000000 0.000000 | 0.000000 0.000000 1.000000 | 0.000000 0.000000 −0.541000 |
| 1 | 1.000000 0.000000 0.000000 | 0.000000 1.000000 0.000000 | 0.000000 0.000000 1.000000 | 0.000000 0.000000 0.000000 |
| 2 | 1.000000 0.000000 0.000000 | 0.000000 1.000000 0.000000 | 0.000000 0.000000 1.000000 | 0.000000 0.000000 0.131929 |
| 3 | 1.000000 0.000000 0.000000 | 0.000000 1.000000 0.000000 | 0.000000 0.000000 1.000000 | 0.000000 0.000000 0.133323 |
| 4 | 1.000000 0.000000 0.000000 | 0.000000 1.000000 0.000000 | 0.000000 0.000000 1.000000 | 0.000000 0.000000 0.383323 |
| 5 | 1.000000 0.000000 0.000000 | 0.000000 1.000000 0.000000 | 0.000000 0.000000 1.000000 | 0.000000 0.000000 2.936493 |
| 6 | 1.000000 0.000000 0.000000 | 0.000000 1.000000 0.000000 | 0.000000 0.000000 1.000000 | 0.000000 0.000000 5.876493 |
| 7 | 1.000000 0.000000 0.000000 | 0.000000 1.000000 0.000000 | 0.000000 0.000000 1.000000 | 0.000000 0.000000 8.376493 |
| 8 | 1.000000 0.000000 0.000000 | 0.000000 1.000000 0.000000 | 0.000000 0.000000 1.000000 | 0.000000 0.000000 10.876493 |
| 9 | 1.000000 0.000000 0.000000 | 0.000000 1.000000 0.000000 | 0.000000 0.000000 1.000000 | 0.000000 0.000000 13.376493 |
| 10 | 1.000000 0.000000 0.000000 | 0.000000 1.000000 0.000000 | 0.000000 0.000000 1.000000 | 0.000000 0.000000 15.876493 |
| 11 | 1.000000 0.000000 0.000000 | 0.000000 1.000000 0.000000 | 0.000000 0.000000 1.000000 | 0.000000 0.000000 127.076493 |

TABLE I-continued

ELEMENT VOLUME DATA:

Values are only accurate for plane and spherical surfaces.
Element volumes are computed by assuming edges are squared up to the larger of the front and back radial aperture.
Single elements that are duplicated in the Lens Data Editor for ray tracing purposes may be listed more than once yielding incorrect total mass estimates.

|  |  | Volume cc | Density g/cc | Mass 9 |
|---|---|---|---|---|
| Element surf | 3 to 4 | 0.001280 | 2.510000 | 0.003212 |
| Total Mass: |  |  |  | 0.003212 |

CARDINAL POINTS:

Object space positions are measured with respect to surface 1.
Image space positions are measured with respect to the image surface.
The index in both the object space and image space is considered.

| W = 0.680000 (Primary) | Object Space | Image Space |
|---|---|---|
| Focal Length | 1.487864 | −1.487864 |
| Principal Planes | −1.570563 | −4.242932 |
| Nodal Planes | −1.570563 | −4.242932 |
| Focal Planes | −0.082700 | −5.730796 |
| Anti-Nodal Planes | 1.405164 | −7.218660 |

End of Table I

Now that it has been disclosed that the beam from the strip diode laser can be effectively collimated and shaped with several different sets of lenses, those skilled in the art can devise other lens sets that can do the same The invention results in a particle counter having a laser intensity of one watt or more in which essentially all noise, except the background noise of the fluid molecules, is eliminated. The particle counter according to the invention typically permits the detection of contaminant particles as small as 0.1 micron in diameter in a 1 cubic foot per minute (CFM) flow of air.

The orientation of the laser and other parts of the system selected to make the shaping of the beam and analysis of the scattering manageable results in the polarization of the laser beam being in a non-optimum direction. The laser is oriented so that it has TM polarization; that is, the magnetic field is along the X-axis. For optimum scattering, the TE polarization mode should be along the X-axis. Therefore, a retarder 114 is included in beam shaping optics 113. Retarder 114 is preferably a one-half wave plate axially aligned with laser beam 121 which rotates the polarization 90 degrees so that the TE mode is along the X-axis.

Turning to FIG. 3, a simplified and partially modified cross-section of the system of FIG. 1 taken through the lines 3—3 of FIG. 2 is shown. In this figure, the optical elements are not shown since they have been described in FIGS. 1 and 2. This figure focuses on the interior elements of flow chamber assembly 102 in which the light scattering from the particles occurs. Elements of the flow chamber assembly that are conventional and do not form a part of the invention have not been included, and the size, shape and location of the various parts have been slightly modified from what they would be in a pure cross-sectional view to make them more distinct, separable and understandable. In addition to the components mentioned above, flow chamber assembly 102 includes fluid sample inlet 302, inlet jet 303 having a jet tip 301, fluid exhaust tube 304, exhaust tube inlet 306, fluid sample exhaust outlet 308, and particle counter output system 310 which includes primary scattered light collector assembly 320, large area scattered light collector assembly 330, and preamplifier assembly 350. Primary collector 320 includes primary light collection optics 312, detector 326 and detector socket 314. Primary light collection optics 312 preferably comprises parabolic mirrors 316 and 317, field flattening optics assembly 318, aperture 323, and light absorption ring 324. Large area scattered light detector 330 includes detector support 331 and large area detector 332. Preamplifier assembly 350 includes an electronic circuit board 353 including chips such as 354, heat sink elements 170 and a thermal compound 356 between the circuit board 353 and heat sink elements 170. The exit opening of fluid jet tip 301 is preferably ten millimeters (mm) in the Z direction, i.e., the horizontal direction in FIG. 3, and 1 mm in the Y direction, i.e., the direction in and out of the paper in FIG. 3. Jet 303 is made of aluminum, which is etched for dullness, and then black anodized and coated with an infrared absorbing paint.

Figure 4:
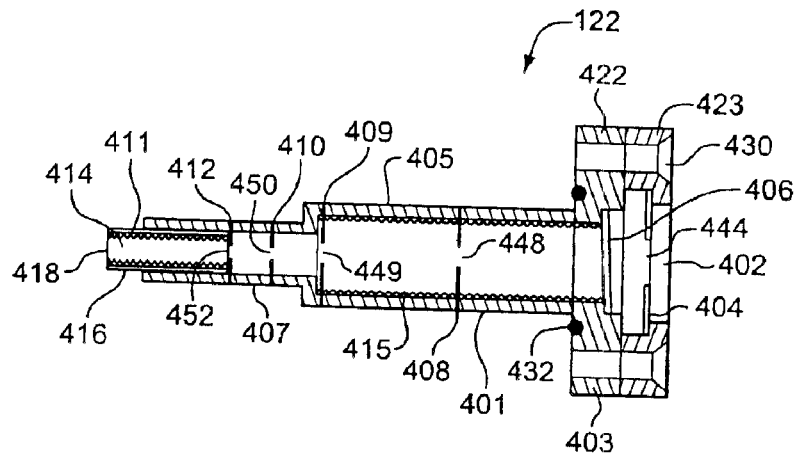
FIG. 4 is a side cross-sectional view of a laser aperture assembly of the system of FIG. 1.
Figure 5:
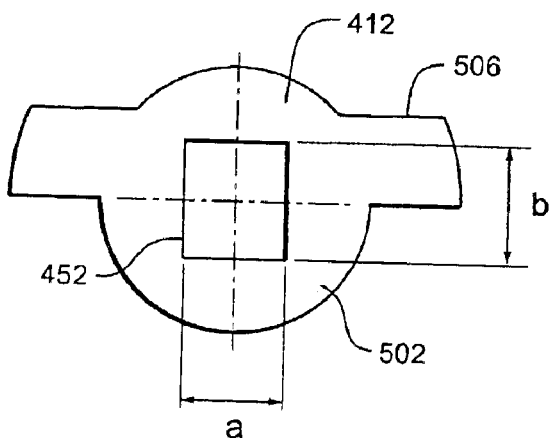
FIG. 5 is a plane view of an aperture plate of FIG. 4.

FIG. 4 is a side cross-sectional view of a laser aperture assembly 122 of the system of FIG. 1, while FIG. 5 is a plane view of fifth aperture plate 412 of FIG. 5. Aperture assembly 122 includes an aperture housing 401, having a head portion 403, a first tube portion 405, a second tube portion 407 preferably having a diameter smaller than that of portion 405, and a cascaded aperture tube 416 preferably having a diameter smaller than that of second portion 407. Assembly 122 also includes first aperture plate 404, entrance window 406, second aperture plate 408, third aperture plate 409, fourth aperture plate 410, fifth aperture plate 412, light stops 415 and cascaded aperture 411. In the preferred embodiment, head portion 403 and tubes 405, 407 and 416 are cylindrical, though they may be rectangular or have a variety of shapes. Head portion 403 is formed in two pieces 422 and 423. The two pieces of the head portion and the head portion and tubes are preferably glued together, though they may be fastened in other ways. Cascaded aperture tube 416 preferably fits flush against fifth aperture plate 412. Head portion 403 preferably includes two screw bores 430 used in attaching aperture assembly 122 to flow chamber housing 120. An O-ring 432 seals the juncture. As known in the art, O-ring 432 sits in a groove in piece 422, though this is not shown for clarity. Entrance window 406 is also glued in place, and is at a slight angle of a few degrees to the perpendicular through the axis of assembly 122 to prevent it from reflecting light back into the laser cavity. First aperture plate 404 is also glued in place, while aperture plates 408, 409, 410, and 412 are fit into slots in housing 401. Light stops 415 and cascaded aperture 411 are preferably formed by tapping threads into the interior surfaces of tubes 405 and 416, respectively. Aperture plate 412 is shown in FIG. 5 to illustrate the shape of this plate as well as plates 408, 409, and 410. Each of these aperture plates include a disk 502 having a pair of flanges 506 which fit into corresponding slots in housing 401. Each has an aperture, such as 452, in the center of the plate. Preferably, the apertures are rectangular. First aperture plate 404 is of the same form, but without flanges 506. As indicated in FIG. 2, laser beam 121 passes through aperture assembly 122 from right to left in FIG. 4, from entrance opening 402, to first aperture 444, to entrance window 406, and then through apertures 448, 449, 450, 452 and cascaded aperture tube 416 in order, to exit opening 418.

All parts of aperture assembly housing 401 are preferably made of black anodized aluminum, unless otherwise noted, though other suitable metals, plastics or other materials may be used. Interior surfaces are preferably painted with a suitable infrared absorbent paint, such as Cardinal Velvethane™. Aperture plates 404, 408, 409, 410 and 412 are made of 0.005 inch thick aluminum and etched to obtain a dull surface before being black anodized. The apertures preferably have the following dimensions in inches, with the dimension a of FIG. 5 given first, and the dimension b of FIG. 5 given second: first aperture 444: 0.118×0.098; second aperture 448: 0.102×0.091; third aperture 449: 0.079×0.091; fourth aperture 450: 0.059×0.071; and fifth aperture 452: 0.059×0.071. Preferably, tube 405 has an interior bore diameter of 0.316 inches, and the threads of light stops 415 are UNS-40 3B. Preferably, tube 411 has an interior bore diameter of 0.1282 inches, and the threads of cascaded aperture 416 are UN28 6-40. In the preferred embodiment, the distances of the apertures from entrance opening 402 in inches are as follows: first aperture 444: 0.051; second aperture 448: 0.670; third aperture 449: 1.235; fourth aperture 450: 1.435 inches; and fifth aperture 452: 1.612 inches.

Figure 6:
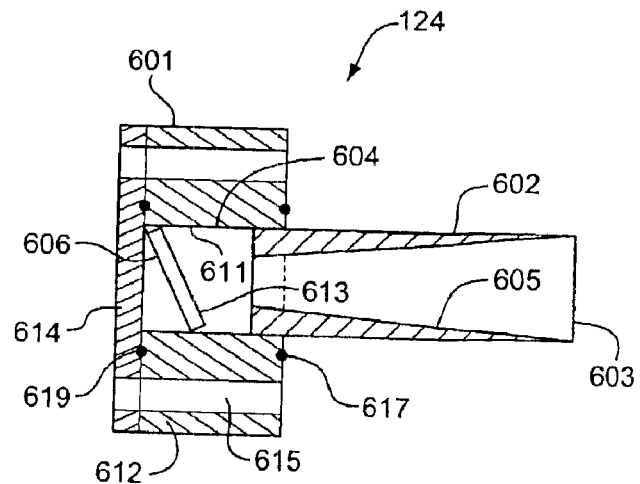
FIG. 6 is a side cross-sectional view of a beam stop assembly of the system of FIG. 1.

FIG. 6 is a side cross-sectional view of a beam stop assembly 124 of the system of FIG. 1. Beam stop assembly 124 includes an absorption chamber housing 601 and a light funneling tube 602 having a laser beam entrance 603. Housing 601 is made in two pieces, 612 and 614. Again, it includes screw bores 615 for attaching assembly 124 to flow chamber housing 120, and O-rings 617 and 619 for sealing the interface between housing 601 and housing 120 and the interface between pieces 614 and 612, respectively, with the conventional O-ring grooves not shown for clarity. Absorption chamber housing 601 includes an absorption chamber 604 in which a beam stop 606 is located at an angle such that any reflections from surface 613 will be directed toward absorption chamber wall 611. The parts of housing 601 are preferably made of aluminum with the exteriors preferably black anodized and painted with an infrared absorbing paint. Tube 602 and housing part 612 are preferably glued together. Inner wall 605 of funnel 602 is preferably polished, while the walls of absorption chamber 604 are preferably etched, black anodized, and painted with an infrared absorbing paint. Beam stop 606 is made of highly infrared absorbent black shot NG1 AR coated glass, though other materials and/or coatings may be used.

Turning to FIGS. 2–7, particle counter 100 according to the invention operates as follows. A source of fluid, which is preferably a gas in the particle counter according to the invention, and typically air, is connected to fluid sample inlet 302. The fluid is carefully guided through fluid inlet assembly 126 and fluid inlet jet 303 to produce a jet 720 (FIG. 7) of fluid flowing from jet tip 301 to exhaust tube inlet 306. In the preferred embodiment, the flow has a high Reynolds number, and thus is turbulent rather than laminar flow. The fluid passes through exhaust tube 304 to exhaust outlet 308 to which a pump or other vacuum source may be attached. The pressures at inlet 302 and outlet 308 are controlled to create a stable flow of fluid from tip 301 to inlet 306.

Laser diode 105 creates laser beam 121 which passes through first lens 109, second lens 111, retarder 114, third lens 116, aperture assembly 122 to fluid flow 720. Any particles in flow 720 scatter a small amount of laser light 121 and the rest of beam 121 passes to beam stop 124 where it is absorbed. The laser and optics 113 may be adjusted via adjusters 106, 110, 112 and 118 to focus beam 121 and optimize the shape and position of beam 121 at flow 720, the characteristics of which will be discussed in detail below. Aperture assembly 122 plays an important role in removing noise, such as noise from spontaneous emission, from beam 121. First aperture 444 masks the beam to remove most of the noise, but creates an undesirable diffraction pattern. Second aperture 448 absorbs the diffraction pattern from the first aperture, but creates its own undesirable diffraction pattern, which is significantly less intense than the diffraction pattern from first aperture 444. Each subsequent aperture masks the diffraction from the previous aperture, and creates a reduced diffraction pattern of its own. Finally, the threads 411 of cascaded aperture tube 416 act as a series of apertures each removing the diffraction of the previous. Threads 415 do not act as apertures but as light stops to block any undesirable light that may originate from entrance window 406, aperture plates 408, 409,410 and 412, or other surfaces. Aperture assembly 122 removes all but 1% of the spontaneous emission noise and other light noise from laser beam 121.

When the light of the laser beam strikes a particle in flow 720, light is scattered in all directions. For particles larger than the wavelength of the laser light, i.e., particles of a micron or larger, the intensity of the light is different in different directions, but for particles of the size of interest herein, i.e., particles in the range of about 0.5 to 0.1 microns, the scattering intensity is essentially the same in all directions. Thus, the scattered light from the particle can be observed from any direction. It is of interest to collect as much of the scattered light as possible, but physical constraints, such as the need for optics to create the light, the need for a fluid source 303, and the need to absorb the portion of the laser beam not scattered, limit the angular range over which light can be collected. In the particle counter according to the invention, scattered light is collected through an angle of 120°; i.e., in a cone of about 60° about a line connecting the center of jet tip 301 and the center of detector 326. The scattered light in this cone passes through opening 319 (FIG. 3) in parabolic mirror 316, is reflected off of parabolic mirror 317, thence to mirror 316 which focuses the light toward detector 326. Field flattening optics 318 shape the image of collected scattered light to better fit the shape of detector 326. Light absorption ring 324 is preferably disposed about the periphery of mirrors 316 and 317 to absorb any stray light that may enter opening 319 not originating from particles. As known in the art, the parabolic mirror system 316 and 317 image the particle on the detector so as much light from the particle as possible hits detector 326. Detector 326 is preferably a photo detector array such as described in U.S. Pat. No. 5,282,151 issued Jan. 25, 1994 to Robert G. Knollenberg, which is hereby incorporated by reference as though fully disclosed herein. Additional light is collected by large area detector 332. As known in the art, Mie scattering calculations lead to multiple values for larger particles. Large area detector 332 is useful in sorting out these multiple values and in general increasing the dynamic range of the particle counter, that is permitting it to detect larger particles as well as small ones. Large area detector 332 is preferably a 10 mm×20 mm rectangular photodiode. The light that strikes detectors 326 and 332 is converted to an electrical signal which is processed by preamplifier electronics on circuit board 353 as known in the art. As known in the art, the output of preamplifier circuit 350 is typically sent to a computer system which processes the signal to typically provide a sound alarm and a visual output showing the number of particles counted in a number of size ranges, referred to as channels in the art. The number of channels and size range of each channel is typically selectable by the user.

While the preferred embodiment of the invention uses a pair of parabolic mirrors in the collection optics, a wide variety of other collection systems may be used. As known in the art, other types of mirrors and lenses may be used alone or in combination to perform essentially the same function as parabolic mirrors 316 and 317. Different detectors may also be used. The flow of fluid may be directed differently, and the direction of the laser beam may be different.

Turning now to FIGS. 7–10, various features of the system according to the invention, particularly laser beam 121, are shown. FIG. 7 is a side diagrammatic view of a portion of laser beam 121 positioned next to inlet jet tip 301 according to a preferred embodiment of the present invention. Beam 121 originates at laser 105, is shaped by beam shaping optics 113, passes tip 301, and the portion of the beam that is not scattered, which is the vast majority of the beam, is adsorbed by beam stop assembly 124. The fluid flow from the jet flow is illustrated by arrows 720. A particle is shown at 710, with the arrows about the particle illustrating the scattered light which is going in all directions. The collection optics is illustrated by a lens 712, and the detector is shown at 326. The various parts of FIG. 7 are extremely out of scale, since, if the figure was to scale, the laser beam would be too small to see, and the optics would not fit on the paper. Further, the collector optics 712 is not intended to depict any particular collector optics, but simply represents any type of collector optics as may be used, including that of the preferred embodiment which uses two mirrors 316 and 317 and a lens 318. As is typical in the art, laser beam 121 has an hour class shape as it passes tip 301, since it is being focused to be as thin, i.e., as dense, as possible where the particles pass through it. The dimension "a" is the thickness of laser beam 121 at the waist 703 in the X direction. The dimension "b" is the thickness of laser beam 121 at ends 730, 731 of jet 301. The dimension "c" is the distance of axis 736 of laser beam 121 from leading edge 738 of jet tip 301. Dotted line 742 is intended to illustrate the collection of light from a small volume at the middle of fluid flow 720 far from jet tip 301, as would occur for an in-situ particle counter. Dashed line 740 is intended to illustrate the collection of light from a volume that includes the entire volume of fluid flow 720 as would occur for a volumetric particle counter. These lines are not intended to depict actual rays in a collection optics, as that is much more complicated. The preferred embodiment of the invention collects light from the entire volume of the $1/e^2$ illuminated fluid flow 720, and thus it is a volumetric particle counter. If the monitoring region is defined as the intersection of the region from which the collection optics collects light with the $1/e^2$ illumination region of the laser, the monitoring region of the preferred embodiment of the invention is the intersection of the $1/e^2$ illumination region of the laser with the entire fluid flow. However, the invention also greatly improves in-situ particle counters and non-in-situ particle counters other than volumetric particle counters.

FIG. 8 illustrates a head-on view of the laser beam at five positions as it passes tip 301: at waist 703, designated the "zero" position; at edge 730 of tip 301, which is 5 mm before the zero position; at the midpoint between waist 703 and edge 730, which is 2.5 mm before the zero position; at the midpoint between waist 703 and edge 731, which is 2.5 mm past the zero position; and at edge 731, which is 5 mm past the zero position.

FIG. 9 is a graph showing the energy distribution 905 of the laser beam along the X-axis in terms of distance from Z-axis 736 versus relative intensity, as compared to the intensity at Z-axis 736. The 80% intensity line 930, the 50% intensity line 920, and the 13.5%, i.e., $1/e^2$, line 910 are shown. The measured width at the three lines are shown to the right of the graph: at the 80% intensity level the width was 12 microns; at the 50% level the width was 21 microns; and at the 13.5% level the width was 35 microns. Conventionally, in the particle counter art, the width of the laser beam is given as the $1/e^2$ or 13.5% width. FIG. 10 is a graph showing the energy distribution 1005 of the laser beam along the Y-axis in terms of the distance from the center of the laser beam, which corresponds to the center of tip 301, versus the relative intensity as compared to the intensity at the center. Again, the 80% intensity line 1030, the 50% intensity line 1020, and the 13.5%, i.e., $1/e^2$, line 1010 are shown. The measured width at the three lines are shown to the right of the graph: at the 80% intensity level the width was 585 microns; at the 50% level the width was 780 microns; and at the 13.5% level the width was 1025 microns. Since the height of the opening in jet tip 301 in the Y-direction, i.e., the direction into and out of the paper in FIG. 7, is 1 mm which is equal to 1000 microns, the $1/e^2$ width of the laser beam in the Y direction is just slightly bigger than the thickness of fluid flow 720, which permits all of the flow volume to be monitored.

An important feature of the invention is that beam shaping optics 113 shapes laser beam 121 from strip laser 105 so that it can be used effectively in a particle counter. To better understand how this occurs, recall that, as mentioned in the Background Of The Invention, light scattered from the physical objects that create the flow, such as jet inlet tip 301, creates noise in the output, which noise prevents detection of extremely small particles. This noise comes from the fact that it is impossible to create laser beams that have a finite width. In discussing FIG. 7, we stated that the hourglass shape of laser beam 121 defined the width of the laser beam. However, this is only the $1/e^2$ width. The laser beam actually continues to fall off below $1/e^2$ line 910 as shown in FIG. 9. In actuality, the laser beam never goes to zero, but continues out to infinity, but practically, beyond a certain distance from the center, it is too small to measure. For example, in FIG. 9, tail 911 extends out to 75 microns from center 907 of the laser beam. However, the part between the $1/e^2$ distance and point where the laser beam intensity is too small to measure does have physical effects. As can be seen from FIG. 7, if the laser beam is too close to jet tip 301, this "tail" of the laser beam will scatter off tip 301, and some of the scattered light will get into the monitoring region of collecting optics 712.

This can be reduced or avoided by locating laser beam 121 far from jet tip 301, but the farther from jet tip 301, the more flow 720 becomes disorganized, and the more there is a chance that the particles measured do not accurately represent those in the sample. This can also be reduced significantly by focusing the collecting optics on a small region of laser beam 121 far from jet tip 301, as in an in-situ system, but this results in increased time to determine undesirable contamination levels. As will be seen in more detail below, the invention overcomes this problem by strongly focusing laser beam 121 so that tail 911 is very small, and then aperturing the remaining intensity level with the aperture assembly 122. This allows laser beam 121 to be placed very close to jet tip 301 without creating significant scattering from the tip.

It is also desirable to have the intensity profile of the laser beam in the Y-direction, that is along the height of flow 720, to be as close to a square wave as possible. If the laser beam profile were square along the height of the beam, this means that the intensity would be uniform all along the height. The result is that particles near the edge of the beam would scatter just as much light as particles near the center of the beam. Since the particle counter determines the size of a particle from the intensity of the scattered light, this permits the size of all particles to be accurately determined. In state-of-the-art particle counters, the difference in intensity of scattering by particles in the center and the edge of the laser beam can be offset to a degree by using a detector array, but it is still important to have as uniform a light beam as possible in the Y direction.

As mentioned above, one important aspect is that laser 105 and beam shaping optics assembly 113 are configured so that along the vertical axis of laser beam 121 in the view of FIG. 7, i.e., the X-axis, the beam is single mode and so that multiple modes are limited to the Y-axis, that is, the axis into and out of the paper in FIG. 7. Since the single mode can be controlled and shaped much more easily than multiple modes, this allows the optics to strongly pinch the laser beam along the X-axis. Fluid flow 720, and thus the particle flow, is in the X direction. To effectively detect particles, the intensity of light in the beam should be as great as possible. Thus, the beam should be as narrow as possible along the X-axis. A feature of the invention is that the $1/e^2$ width of the beam at the waist of the laser beam, i.e., distance "a", is 75 microns or less, and preferably, 50 microns of less. In the preferred embodiment, it is 35 microns. This width is as good or better than the $1/e^2$ width of particle counters with conventional low-power laser diodes having only a $TEM_{00}$ mode. Another feature of the invention is that the center of the beam along the Y-axis, i.e., along the height of jet tip 301, the $1/e^2$ width of the beam at ends 730 and 731, is 200 microns or less; more preferably, this width is 175 microns or less; in the preferred embodiment, it is about 150 microns. It should be noted that this is the maximum divergence of the beam. That is, from FIG. 8, it can be seen that, at the top and bottom of the beam along the Y-axis, the expansion of the beam is not as great as one goes away from the waist. While to one not skilled in the particle counter art it may seem that the expansion of the beam from waist 703 to the portions opposite ends 730 and 731 is large, this is actually typical of the laser beam for particle counters. That is, the performance with the much more powerful strip laser diode is as good as the performance with the conventional lower-power diodes. These features play an important role in the ability to locate the laser beam 121 extremely close to jet tip 301 without creating significant light scattering from the tip. It plays an important role in permitting excellent sensitivity in a volumetric instrument.

Another feature of the invention is that the graph of FIG. 9 is Gaussian. That is, the intensity of the laser beam fall offs in a Gaussian curve. As known in the art, ideally, the graph of FIG. 9 would be a square wave, because the intensity of the beam would then be uniform across the entire width and drop off to zero rapidly. Uniformity across the beam means that the scattering intensity does not change as the particle passes through the beam, and, as discussed above, the rapid drop off means that the scattering of light from tip 301 can be avoided. However, there is no such thing as a square wave intensity profile of a laser beam. The Gaussian profile of beam 121 in the particle counter according to the invention does fall off rapidly, however, so that the laser beam can be located close to jet tip 301 without risking scatter from the tip. It is a feature of the invention that the separation distance "d" of center axis 736 of laser beam 121 from inlet jet tip 301 is 7 mm or less, preferably 5 mm or less. Most preferably, it is 4 mm or less, and in the preferred embodiment, it is about 3.5 millimeters (mm). However, it will be appreciated that different separation distances may be employed for different system configurations and that all such variations are intended to be included within the scope of the present invention.

A further significant feature of the invention is that the graph of FIG. 10 is more uniform than a Gaussian distribution; that is, it is even closer to a square wave than a Gaussian. This curve is, in fact, as ideal an energy density curve as possible with even $TEM_{00}$ mode lasers; thus, the intensity level is about as uniform as possible across the height of the beam. It is surprising that such a good result has been obtained along an axis that includes multiple modes. This uniformity means that particles near the bottom of the beam will reflect close to the same amount of light as particles near the center of the beam, which permits more accurate sizing of particles.

A further important feature of the invention is that the particle counter according to the invention has an output which is substantially free of any noise greater than the noise created by light scattered from molecules of the fluid. That is, the sensitivity of the particle counter is limited only by the noise created by the fluid itself. While this has been accomplished in a few prior art intracavity particle counters, it has never before been accomplished in an extracavity particle counter utilizing such high power. Particularly, this has never been accomplished utilizing a laser diode.

There has been described a novel particle counter system that utilizes a strip laser diode. It should be understood that the particular embodiments shown in the drawings and described within this specification are for purposes of example and should not be construed to limit the invention, which will be described in the claims below. Further, it is evident that those skilled in the art may now make numerous uses and modifications of the specific embodiments described, without departing from the inventive concepts. For example, the light collector, such as 320, may be replaced with a wide variety of other collectors ranging from a simple collector, such as a single photodetector, to very complex systems using a large number of lenses and/or mirrors and/or multiple detectors. It is also evident that the methods recited may in many instances be performed in a different order; or equivalent structures and processes may be substituted for the various structures and processes described. Consequently, the invention is to be construed as embracing each and every novel feature and novel combination of features present in and/or possessed by the invention herein described.

We claim:

1. A device for optically detecting an unconstrained particle suspended in a flowing fluid, said device comprising:
   a sample chamber having a fluid inlet and a fluid outlet;
   a strip laser diode producing a laser beam;
   a beam shaping system directing said laser beam at said flowing fluid in said sample chamber;
   an optical detector located to detect light scattered by said particle in said sample chamber, said detector producing an electric signal characteristic of said scattered light; and
   an output device communicating with said detector to provide an output characteristic of said particle detected in said fluid in said sample chamber.

2. A device as in claim 1 wherein said fluid is a gas.

3. A device as in claim 1 wherein said device is a non-in-situ particle counter.

4. A device as in claim 3 wherein said device is a volumetric particle counter.

5. A device as in claim 2 wherein said beam shaping system comprises a lens.

6. A device as in claim 5 wherein said lens comprises an aspheric collimating lens, an achromatic spherical lens and a cylinder lens.

7. A device as in claim 5 wherein said lens comprises an aspheric collimating lens and two cylinder lenses.

8. A device as in claim 1 wherein said fluid flows in a first direction, said laser beam is single mode in a first dimension substantially along said first direction.

9. A device as in claim 1 wherein said fluid flows in a first direction, said laser beam includes multiple modes in a second dimension substantially along a second direction perpendicular to said first direction.

10. A device as in claim 1 wherein said fluid flows along a first axis, and the energy distribution of said laser beam substantially along said first axis, in terms of distance from the center of the laser beam versus relative intensity as compared to the intensity at the center, is Gaussian.

11. A device as in claim 1 wherein said fluid flows along a first axis, and the energy distribution of said laser beam substantially along a second axis perpendicular to said beam and said first axis, in terms of distance from the center of the laser beam versus relative intensity as compared to the intensity at the center, is more uniform than a Gaussian distribution.

12. A device as in claim 1 wherein said fluid flows along a first axis, and the $1/e^2$ width of said laser beam in the direction of said first axis, at a first point within said fluid flow, is 75 microns or less.

13. A device as in claim 12 wherein said width is 50 microns of less.

14. A device as in claim 12 wherein said width is 40 microns or less.

15. A device as in claim 12 wherein at a second point at the edge of said fluid-flow the $1/e^2$-width of said laser beam in a direction parallel to said first axis is 200 microns or less.

16. A device as in claim 15 wherein said width at said second point is 175 microns or less.

17. A device as in claim 15 wherein said width at said second point is 150 microns or less.

18. A device as in claim 1 wherein said fluid inlet comprises an inlet jet tip from which said fluid flows, and the separation distance of the center of said laser beam from said inlet jet tip is 7 mm or less.

19. A device as in claim 18 wherein said separation distance is 5 mm or less.

20. A device as in claim 19 wherein said separation distance is 4 mm or less.

21. A device as in claim 1 wherein said strip laser diode has a power of 1 watt or greater.

22. A device as in claim 21 wherein said strip laser diode has a power of 2 watts or greater.

23. A device as in claim 1 wherein said output is substantially free of noise greater than the noise created by light scattered from molecules of said fluid.

24. A device for optically detecting an unconstrained particle suspended in a flowing fluid, said device comprising:
   a fluid inlet for producing a fluid flow;
   a strip laser diode producing a laser beam;
   a beam shaping system directing said laser beam at said fluid flow;
   a light collector located to collect light scattered by said particle in fluid flow, said collector producing an electric signal characteristic of said scattered light; and
   an output device communicating with said collector to provide an output characteristic of said particle detected in said fluid.

25. A device for optically detecting an unconstrained particle suspended in a flowing fluid, said device comprising:
   a sample chamber having a fluid inlet and a fluid outlet;
   a laser diode producing a laser beam, said laser diode having at least one dimension of 10 microns or larger;
   a beam shaping system directing said laser beam at said flowing fluid in said sample chamber;
   a light collector located to collect light scattered by said particle in said sample chamber, said collector producing an electric signal characteristic of said scattered light; and
   an output device communicating with said collector to provide an output characteristic of said particle detected in said fluid in said sample chamber.

26. A device as in claim 25 wherein said dimension is 50 microns or greater.

27. A device as in claim 25 wherein said dimension is 100 microns or greater.

28. A device for optically detecting an unconstrained particle suspended in a flowing fluid, said device comprising:
   a fluid inlet for flowing said fluid in a first direction;
   a laser producing a laser beam having multiple modes;
   a beam shaping system directing said multiple mode laser beam at said flowing fluid with said multiple modes constrained to a dimension along a second direction substantially perpendicular to said first direction;
   a light collector located to collect light scattered by said particle in said flowing fluid, said collector producing an electric signal characteristic of said scattered light; and
   an output device communicating with said collector to provide an output characteristic of said particle detected in said fluid flow.

29. A device as in claim 28 wherein said beam shaping system comprises a one-half wave plate.

30. A device as in claim 28 wherein said laser comprises a strip laser diode.

31. A device as in claim 28 wherein said laser includes a laser cavity and said fluid flow is located outside said laser cavity.

32. A method for optically detecting an unconstrained particle suspended in a fluid, said method comprising:

flowing said fluid containing an unconstrained particle;

providing a strip laser diode producing a laser beam having multiple modes;

directing said laser beam at said fluid flow;

collecting light scattered by said particle in said fluid; and providing an output based on said collected light scattered by said particle detected in said flowing fluid.

33. A method as in claim 32 wherein said fluid flows substantially along a first direction, and said providing and directing comprises providing said laser beam and directing it so that said multiple modes occur in a dimension along a second direction perpendicular to said first direction and the direction of said laser beam.

34. A method as in claim 32 wherein said providing and directing comprises providing said laser beam and directing it so that said laser beam is single mode in a first dimension along said first direction.

35. A method as in claim 32 wherein said directing comprises focusing said laser beam with at least two lenses selected from the group consisting of an aspheric collimating lens, an achromatic spherical lens, and a cylinder lens.

36. A method as in claim 32 wherein said directing, collecting and providing an output are performed such that said output is substantially free of noise greater than the noise created by light scattered from molecules of said fluid.

* * * * *